(12) United States Patent  (10) Patent No.: US 7,652,188 B2
Levanon et al.  (45) Date of Patent: Jan. 26, 2010

(54) ADHESIVE BANDAGE WITH DISPLAY

(75) Inventors: Baruch Levanon, Hod-Hasharon (IL); Zvi Nitzan, Zufit (IL); Daniela Mavor, Tel Aviv (IL); Nurit Harel, Tel Aviv (IL)

(73) Assignee: Power Paper Ltd., Beit Shemesh (IL)

( * ) Notice: Subject to any disclaimer, the term of this patent is extended or adjusted under 35 U.S.C. 154(b) by 331 days.

(21) Appl. No.: 10/741,435

(22) Filed: Dec. 22, 2003

(65) Prior Publication Data

US 2005/0010146 A1  Jan. 13, 2005

Related U.S. Application Data

(63) Continuation-in-part of application No. PCT/IL02/00489, filed on Jun. 20, 2002.

(60) Provisional application No. 60/299,191, filed on Jun. 20, 2001.

(51) Int. Cl.
   *A61F 13/00*  (2006.01)

(52) U.S. Cl. ............... 602/41; 600/306; 602/52; 602/42

(58) Field of Classification Search ............... 604/20, 604/21, 890.1; 607/149, 151, 1; 602/41, 602/42, 52, 54, 56; 424/447, 448; 600/301, 600/306, 307
   See application file for complete search history.

(56) References Cited

U.S. PATENT DOCUMENTS

| 4,149,662 | A | * | 4/1979 | Ramaciere | 224/164 |
|---|---|---|---|---|---|
| 4,331,161 | A | * | 5/1982 | Patel | 600/549 |
| 4,708,716 | A | * | 11/1987 | Sibalis | 604/20 |
| 5,050,612 | A | * | 9/1991 | Matsumura | 600/483 |
| 5,897,522 | A |   | 4/1999 | Nitzan | |
| 5,984,874 | A | * | 11/1999 | Cerwin | 600/549 |
| 6,018,673 | A | * | 1/2000 | Chin et al. | 600/322 |
| 6,129,696 | A | * | 10/2000 | Sibalis | 604/20 |
| 6,686,843 | B2 | * | 2/2004 | Felkowitz | 340/573.1 |
| 6,847,913 | B2 | * | 1/2005 | Wigley et al. | 702/131 |
| 7,204,832 | B2 | * | 4/2007 | Altshuler et al. | 606/9 |
| 7,304,201 | B2 | * | 12/2007 | Holloway et al. | 602/41 |
| 2002/0082668 | A1 |   | 6/2002 | Ingman | |

FOREIGN PATENT DOCUMENTS

WO  WO 02/102273  12/2002

\* cited by examiner

*Primary Examiner*—Patricia M Bianco
*Assistant Examiner*—Camtu T Nguyen
(74) *Attorney, Agent, or Firm*—Kenyon & Kenyon LLP

(57) ABSTRACT

An adhesive bandage is provided. The adhesive bandage includes: (a) an absorbent pad having an absorbent surface; (b) an adhesive tape attached to the absorbent pad, the adhesive tape being configured for attaching to a skin region so as to position the absorbent surface against a portion of the skin region; (c) a display being positioned on an outer surface of the adhesive bandage the display being configured and positioned so as to be viewable by an individual when the adhesive tape is attached to the skin region; and (d) a power source attached to or integrated with the adhesive tape, the power source being for powering the display, the display being for increasing an acceptability of use of the adhesive bandage by the individual when powered. Furthermore, the present invention provides an adhesive bandage with a display, the display being for displaying a skin condition value and for increasing an acceptability of use of the adhesive bandage by the individual when powered.

11 Claims, 3 Drawing Sheets

ADHESIVE BANDAGE WITH DISPLAY

This application is a continuation in part of PCT patent application No. PCT/IL02/00489, filed Jun. 20, 2002, which claims priority from U.S. Provisional Application No. 60/299,191, filed Jun. 20, 2001, now expired.

FIELD AND BACKGROUND OF THE INVENTION

The present invention relates to an adhesive bandage which includes a power source and a display, such as an LED display for encouraging use thereof by individuals and in particular children or other individuals.

Bandages, and in particular adhesive bandages such as those sold under the trademark BAND-AID are widely used by both children and adults.

Adhesive bandages typically include a pad of gauze or similar absorbent material positioned at a center of a strip of adhesive tape. When applied, the pad is positioned over a wound and secured to the skin via the adhesive tape.

Adhesive bandages made for children are oftentimes decorated with patterns, colors or animation characters in order to increase the attractiveness of such bandages and as a result the likelihood that children will use them.

However, notwithstanding the attempts to increase the attractiveness of such adhesive bandages, there still exists a problem in encouraging the use of such bandages for their desired protective function when necessary, particularly by children.

There is thus a widely recognized need for, and it would be highly advantageous to have, a bandage such as an adhesive bandage configured with an electronic display which serves to increase the acceptability of use of the adhesive bandage by individuals and in particular children or young adults.

SUMMARY OF THE INVENTION

According to one embodiment of the present invention there is provided an adhesive bandage including: (a) an absorbent pad having an absorbent surface; (b) an adhesive tape attached to the absorbent pad, the adhesive tape being configured for attaching to a skin region so as to position the absorbent surface against a portion of the skin region; (c) a display being positioned on an outer surface of the adhesive bandage, the display being configured and positioned so as to be viewable by an individual when the adhesive tape is attached to the skin region; and (d) a power source attached to or integrated with the adhesive tape, the power source being for powering the display, the display being for increasing an acceptability of use of the adhesive bandage by the individual when powered.

According to further features in preferred embodiments of the invention described below, the display includes at least one light emitting diode (LED).

According to still further features in the described preferred embodiments the power source is a flexible thin layer liquid state electrochemical cell.

According to still further features in the described preferred embodiments the flexible thin layer liquid state electrochemical cell includes a first layer of insoluble negative pole, a second layer of insoluble positive pole and a third layer of aqueous electrolyte, the third layer being disposed between the first and second layers.

According to still further features in the described preferred embodiments the flexible thin layer liquid state electrochemical cell is an open cell, and further wherein the third layer includes: (i) a deliquescent material for keeping the open cell wet at all times; (ii) an electroactive soluble material for obtaining required ionic conductivity; and (iii) a water-soluble polymer for obtaining a required viscosity for adhering the first and second layers to the third layer.

According to still further features in the described preferred embodiments the adhesive bandage further includes control circuits for controlling power provision from the power source to the display.

In a preferred embodiment the adhesive bandage further includes a skin condition detector.

In a preferred embodiment the skin condition detector detects and evaluates a skin condition.

In a preferred embodiment the skin condition is selected from at least one of the group consisting of acidity (pH), moisture (water content), fat (sebum) content, elasticity, barrier function of skin (impermeability), skin resistance, skin conductance, scarring, pigmentation, melanin and erythrema index, transepidermal water loss, skin roughness, acne, bacteria, fungal and viral contamination and any combination thereof.

In a preferred embodiment the display readily facilitates displaying a skin condition value.

In a preferred embodiment the display is selected from at least one of the group consisting of numerical display, text display, graphical display, light display and any combination thereof.

In a preferred embodiment the adhesive bandage further includes a sound device.

In a preferred embodiment the adhesive tape is reusable.

In a preferred embodiment the display is selected from at least one of the group consisting of all types of LCD display, polymer LCD display, LED display, VFD, fluorescent displays, organic displays, incandescent and neon display and illuminescence type display and any combination thereof.

In a preferred embodiment the adhesive bandage is reusable.

In a preferred embodiment the adhesive bandage is for use in wound treatment.

In a preferred embodiment the adhesive bandage is for use in detection, treatment and evaluation of dermatological and cosmetic skin conditions.

In a second embodiment the present invention provides an adhesive bandage including: (a) a pad having a protective surface; (b) an adhesive tape attached to the pad, the adhesive tape being configured for attaching to a skin region so as to position the surface against a portion of the skin region; (c) a display being positioned on an outer surface of the adhesive bandage, the display being configured and positioned so as to be viewable by an individual when the adhesive tape is attached to the skin region; (d) a skin condition detector in contact with said skin region and said display, said skin condition detector being configured for detecting and evaluating a skin condition; and (e) a power source attached to or integrated with the adhesive tape, the power source being for powering the display, the display being for increasing an acceptability of use of the adhesive bandage by the individual when powered and for displaying a skin condition value.

In a preferred embodiment the pad is non-absorbent.

In a preferred embodiment the pad is absorbent.

In a preferred embodiment the skin condition is selected from at least one of the group consisting of acidity (pH), moisture (water content), fat (sebum) content, elasticity, barrier function of skin (impermeability), skin resistance, skin conductance, scarring, pigmentation, melanin and erythrema index, transepidermal water loss, skin roughness, acne, bacteria, fungal and viral content and any combination thereof. In a third embodiment the present invention provides an adhesive bandage including: (a) an absorbent pad having an absorbent surface; (b) an adhesive tape attached to the absorbent pad, the adhesive tape being configured for attaching to a skin region so as to position the absorbent surface against a portion of the skin region; (c) a display being positioned on an outer surface of the adhesive bandage, the display being configured and positioned so as to be viewable by an individual when the adhesive tape is attached to the skin region; and (d) a power source attached to or integrated with the adhesive tape, the power source being for powering the display, the display being for displaying a skin condition parameter.

As used herein the term 'bandage' includes, but is not limited to a pad of gauze or similar absorbent material. The term includes a patch of any suitable material to be placed on a specific area of the skin or body, including absorbent and non-absorbent materials. The term also includes, but is not limited to, a bandage of any type to be placed on the skin or body for any suitable purpose, such as but not limited to wound care, protection of wound, treatment of a skin abnormality, protection of a skin abnormality, diagnosis of a skin condition and treatment of a skin condition.

As used herein the term 'adhesive bandage' includes, but is not limited to, a bandage positioned at a center of a strip of adhesive material, such as, but not limed to tape. Preferably, the adhesive material secures the bandage to the skin. The term includes any suitable adhesive material. Furthermore, the term includes one-time use and reusable adhesive material.

As used herein the term 'skin condition' includes, but is not limited to, any suitable physical or non-physical characteristic associated with skin. Examples of skin conditions include, but are not limited to acidity (pH), moisture (water content), fat (sebum) content, elasticity, barrier function of skin (impermeability), skin resistance, skin conductance, scarring, pigmentation, melanin and erythrema index, transepidermal water loss, skin roughness, acne, bacteria, fungal and viral contamination.

As used herein the term 'skin condition value' includes, but is not limited to, any suitable value, which quantitates or qualitates the skin condition. The term includes numerical values and non-numerical values. The term further includes comparative values, such as, but not limited to comparing to previous, standard or optimum values.

The present invention successfully addresses the shortcomings of the presently known configurations by providing a bandage such as an adhesive bandage, which includes an electronic display capable of encouraging use of the bandage by children and other individuals.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
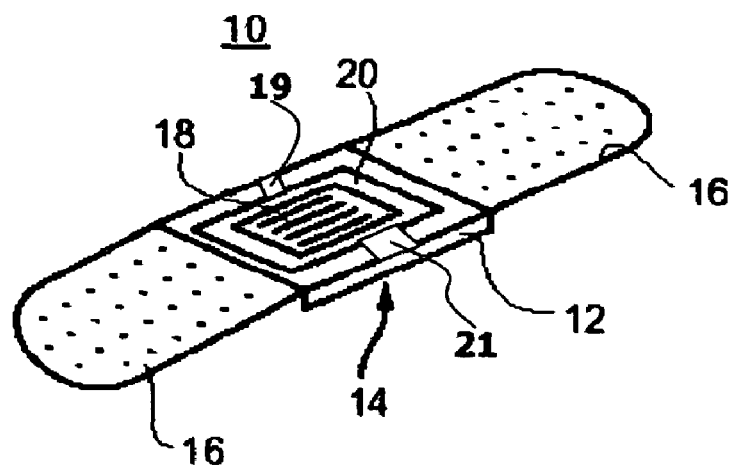
FIG. 1 is an adhesive bandage constructed in accordance with the teachings of the present invention.

The present invention is of a bandage such as an adhesive bandage, which includes a powered display, which can be used to increase the attractiveness of the bandage to a user, such as a child or other individual, thus increasing the likelihood of use thereby. Furthermore, the present invention is of a bandage, which includes a powered display, wherein the display displays information. Preferably, the displayed information includes skin condition parameters and values. Still further, the present invention is of an adhesive bandage, which includes a powered display, wherein the display is for displaying skin condition values and for increasing the acceptability of a bandage to a user.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Although colorful or patterned adhesive bandages are better accepted by children as opposed to clear or flesh colored bandages, such decorations are oftentimes not enough to encourage use of bandages by children.

Thus, the present invention provides an adhesive bandage, which is configured for motivating use by an individual and in particular a child, which bandage is referred to hereinunder as bandage 10.

Moreover, devices known in the prior art to quantitate skin condition factors, can be offputting to an individual. The cumbersome devices, which are usually connected or attached to an individual can be frightening. The bandage of the present invention 10, which is configured to display skin condition values on a simple display on the bandage, wherein the display is aesthetically pleasing, encourages use of such a skin condition display bandage.

As is illustrated in FIG. 1, bandage 10 includes a pad 12. Preferably, pad 12 is an absorbent pad 12 having an absorbent surface 14. Preferably, absorbent pad 12 serves for covering a wound, such as a scrape or cut and for absorbing blood or other fluids secreted by the wound. Optionally, absorbent pad 12 readily facilitates covering any area of the body, such as, but not limited to skin for treatment, protection or diagnosis of the skin or skin condition. Absorbent pad 12 typically includes a cotton center surrounded by a sheath made of woven material. Numerous examples of materials suitable for use as absorbent pad 12 are known in the art and as such no further description of such materials is given herein. In an alternative embodiment, a non-absorbent pad 12 is optionally used. Non-absorbent pads 12 typically include a non-absorbing polymer, such as silicone polymer, rubber, polyethylene and polypropylene sheets. Occasioning, that bandage 10 is for use in a dermatological or cosmetic treatment, a non-absorbent pad 12 is preferable.

Bandage 10 further includes an adhesive tape 16, which is preferably attached to absorbent pad 12. Preferably, adhesive tape 16 is constructed from woven or non-woven material coated with adhesive, which is covered by a releasable liner, which is peeled prior to application. Preferably, adhesive tape 16 is constructed from any suitable known type of adhesive material. Optionally, adhesive tape 16 is reusable. Preferably, adhesive tape 16 is fabricated from materials, which allow air passage, such as woven cotton or perforated vinyl.

Adhesive tape 16 serves for attaching bandage 10 to a skin region thereby positioning absorbent surface 14 against a portion of skin region.

Bandage 10 further includes a display 18, which is positioned on an outer surface of bandage 10. Display 18 is configured and positioned so as to be viewable by an individual when bandage 10 is applied to a skin region.

Optionally, display 18 is any suitable type of display 18, which is simple and small enough to be included in bandage 10. Preferably, display 18 is a powered display 18. Suitable examples of powered display 18 include, but are not limited to all types of LCD display, including polymer LCD display, LED display, VFD and other fluorescent displays, organic displays, incandescent and neon display and illuminescence type display. Preferably, display 18 includes one or more light emitting diodes (LEDs), which when activated generate a light pattern, such as for example, a flashing light pattern or graphical, text or numerical values. In a preferred embodiment display 18 generates a display of skin condition values. Preferably, skin conditions include, but are not limited to acidity (pH), moisture (water content), fat (sebum) content, elasticity, barrier function of skin (impermeability), skin resistance, skin conductance, scarring, pigmentation, melanin and erythrema index, transepidermal water loss, skin roughness, acne, bacteria, fungal and viral contamination and any combination thereof.

Optionally, bandage 10 includes a sound device 19, such as but not limited to a device 19, which produces and emits any suitable sound, such as a voice, an alarm, a tune or melody. Any suitable sound device known in the art can be used. Optionally, sound device 19, alerts a user when a skin condition value has been displayed, or if a skin condition value is not in the normal value range or if evaluation is complete. Alternatively, sound device 19 is configured to readily facilitate increased acceptability of bandage 10.

Figure 4:
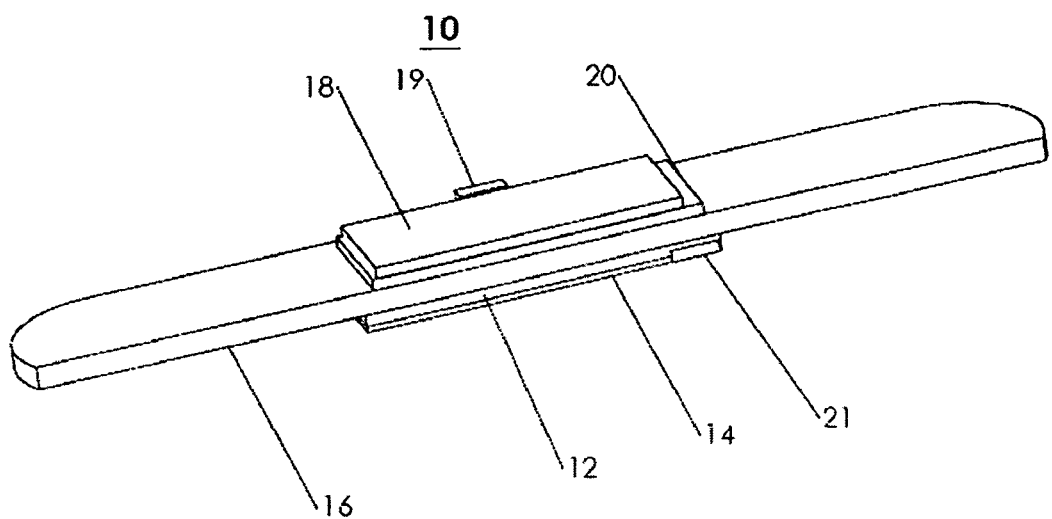
FIG. 4 is a perspective view of the adhesive bandage of FIG. 1.
Figure 5:
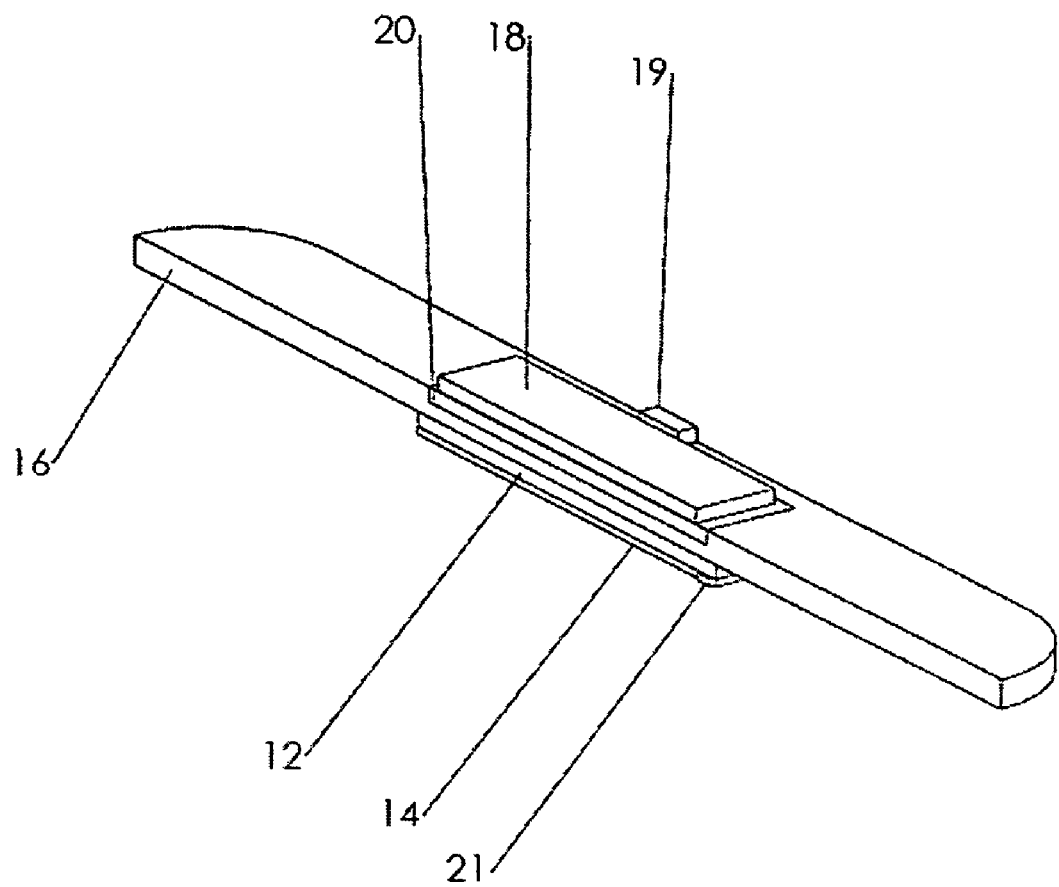
FIG. 5 is an alternative perspective view of the adhesive bandage of FIG. 1.

Bandage 10 further includes a power source 20 which is attached to, or integrated with, adhesive tape 16, as shown in FIG. 4 and FIG. 5. Power source 20 serves for powering display 18 and as such it electrically communicates therewith preferably through control circuitry. Control circuitry preferably includes switches for toggling power supply to display 18 on or off and/or for toggling display 18 between several display modes. Optionally, power source 20 also serves for powering a skin condition detector 21. It will be appreciated that in order to be incorporated within bandage 10, power source 20 must be a relatively small and thin device.

As such, power source 20 is preferably a liquid or solid state thin layer electrochemical cell. Numerous examples of thin layer electrochemical cells exist in the art, and as such no further description is given herein with respect to such electrochemical cells.

Preferably, power source 20 is a liquid state thin layer electrochemical cell of an open cell configuration.

A liquid state open cell thin layer electrochemical cell, which can be used by bandage 10 of the present invention is described hereinafter and in U.S. Pat. No. 5,897,522, the teachings of which are incorporated herein by reference.

The use of an open cell liquid state power source of that type is presently preferred since unlike closed cell liquid state power sources an open cell power source cannot leak and as such it is safer for use in human applications, especially with children. In addition, the open cell configuration enables fabrication of a thinner cell, which is easily incorporated into bandage 10 and yet as the same time, the open cell design enables air flow therethrough and thus ventilation of bandage 10.

Bandage 10 is applied by a user in a manner similar to application of commonly used adhesive bandages. Preferably, to use bandage 10, a user simply removes the protective cover, such as liners from adhesive bandage 16 and applies bandage 10 to a skin region. Display 20 can be activated by the user prior to or following application of bandage 10. Preferably, any suitable method of initiating activation of display can be used.

Optionally, control circuitry of bandage 10 can be configured such that display 18 is automatically activated upon removal of liner, application of bandage 10 to the skin region (e.g., skin contact), or application of pressure to bandage 10.

Once display 18 is activated via power source 20, it displays a display 18. Preferably, display 18 includes at least one, of or a combination of, a text, a graphic design, numerical values and light pattern thus increasing the attractiveness of the bandage to a user, such as a child or other individual, and therefore increasing the likelihood of use thereby. Any type of suitable display 18, which can increase acceptability of bandage 10 can be used in the bandage of the present invention 10.

Preferably, sound device 19, is powered by power source 20. Sound device 19 can be activated by the user prior to or following application of bandage 10. Any suitable method of initiating activation of sound device 19 can be used. Optionally, control circuitry of bandage 10 can be configured such that sound device 19 is automatically activated upon removal of liner, application of bandage 10 to the skin region (e.g., skin contact), or application of pressure to bandage 10. Preferably, sound, such as, but not limited to music readily facilitates increasing the attractiveness of bandage 10, thereby increasing the likelihood of use thereof.

It will be appreciated that control circuitry can be configured such that the light pattern emitted by display 18 responds to user movements and the like, thus leading to an interaction between the user and bandage 10, thereby further increasing the likelihood of use by a child.

In one preferred embodiment, wherein bandage 10 is for use in skin treatment for quantifying a skin condition, bandage 10 optionally includes at least one or a combination of skin condition detector 21. Optionally, any suitable skin condition detector 21 know in the art, which employs any method of detection known in the art, can be used in bandage 10 for detection of any skin condition. Preferably, skin condition detector 21 is selected according to the size constraints of bandage 10. More preferably, skin detector 21 is a micro skin detector 21. Skin condition detectors 21 which can be utilized in bandage 10 of the present invention include, but are not limited to a skin fat (sebum) content detector, skin moisture (water content) detector, skin pH detector, skin elasticity detector, detector of skin impermeability (barrier function), skin resistance detector, skin conductance detector, skin scarring detector, skin pigmentation and melanin and erythrema index detector(s), transepidermal water loss detector, skin roughness detector and skin bacterial, fungal or viral content detector. Examples of a skin moisture detector 21, which can be used in bandage 10 include HC103/HC104, and HC201, Elektronik.

Skin condition detector 21 is configured to readily facilitate detecting and quantitating or qualitating a skin condition. Preferably, skin condition detector 21 is in contact with skin area and attached to power source 20 and display 18. Preferably, power source 20 provides power to skin condition detector when needed. Optionally, skin condition detector 21 can be separately powered. Detected and evaluated skin condition numerical value or qualitative values, such as high, low medium or good, bad, and moderate skin condition can be displayed on display 18. Optionally, more than one skin condition can be evaluated, displayed and compared with old values, standard or optimum values. Optionally, display 18 includes a memory module (not shown in FIG. 1), which is configured to store data, such as, but not limited to former skin condition values and date of skin condition evaluation.

In an alternative embodiment, bandage having display 10 is attachable to fingernails, toe nails or teeth or any other suitable area of the body, to detect and evaluate nail and tooth conditions, such as, but not limited to enamel strength, fungus infection, discolouration, bacterial infection, cavity and plaque content.

Bandage 10 is of any suitable size, length, colour and shape, which is preferably dependent on the use of bandage 10. Preferably, bandage 10 is disposable or reusable.

Figure 2:
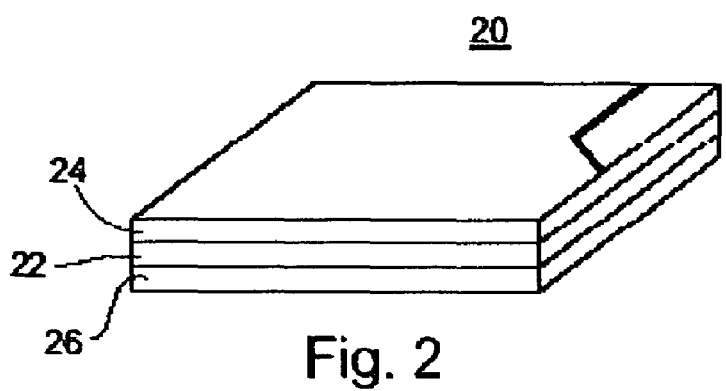
FIG. 2 is a perspective view of a basic configuration of a prior art flexible thin layer open electrochemical cell utilizable by the adhesive bandage of the present invention.

FIG. 2 illustrates a basic configuration of the flexible thin layer open electrochemical cell utilizable as power source 20 by bandage 10 of the present invention, and which is referred to hereinunder as open cell 20.

Open cell 20 includes three layers as follows. A first layer of insoluble negative pole 24, a second layer of insoluble positive pole 26 and a third layer of aqueous electrolyte 22. As used in this document, a discharged negative pole is where an oxidation occurs, whereas the positive pole is where reduction occurs. The aqueous electrolyte layer 22 includes a deliquescent (i.e., hygroscopic) material for keeping open cell 20 wet at all times; an electroactive soluble material for obtaining the required ionic conductivity; and a watersoluble polymer for obtaining the required viscosity for adhering pole layers 24 and 26 to aqueous electrolyte layer 22. Following is a more detailed description of each of layers 24, 26 and 22 and their role in the operation of open cell 20.

Aqueous electrolyte layer 22 typically includes a porous insoluble substance, such as, but not limited to, filter paper, plastic membrane, cellulose membrane, cloth, non-woven material (e.g., cotton fibers), etc., the porous substance is soaked with an aqueous solution including three components: a deliquescent material; an electroactive soluble material; and a water-soluble polymer.

The deliquescent material by being hygroscopic maintains open cell 20 moisturized at all times. The level of moisture within open cell 20 may vary depending on deliquescent material selection, its concentration and ambient humidity. Suitable deliquescent materials include, but are not limited to, calcium-chloride, calcium-bromide, potassium-biphosphate, potassium-acetate and combinations thereof.

The electroactive soluble material is selected in accordance with the materials of which the negative and positive pole layers are made. A list of frequently used electroactive soluble materials suitable for use with open cell 20 includes, for example, zinc-chloride, zinc-bromide and zinc-fluoride for various primary cells and potassium-hydroxide and sulfuric-acid for rechargeable cells. The water-soluble polymer is employed as an adhesive agent to adhere (i.e., glue) pole layers 24 and 26 to the aqueous electrolyte layer 22. Many types of polymers are suitable ones, such as, for example, polyvinylalcohol, poliacrylamide, polyacrylic acid, polyvinylpyrolidone, polyethylenoxide, agar, agarose, starch, hydroxyethylcellulose and combinations and copolymers thereof.

Each of negative and positive pole layers 24 and 26 includes a mix of a suitable (negative or positive, respectively) active insoluble powder material along with an aqueous solution similar to the solution described hereinabove, which includes a deliquescent material; an electroactive soluble material; and a water-soluble polymer.

It is clear to one having ordinary skills in the art that while the electroactive soluble material should not change, the deliquescent material and the water-soluble polymer may be selected otherwise in the later solution, in other words, the electroactive soluble material should be kept the same in all three layers 22, 24 and 26, whereas the deliquescent material and the water-soluble polymer may vary among the layers, according to the specific application.

Appropriate selection of active insoluble powder materials for the negative 24 and positive 26 pole layers with a matching electroactive soluble material, as exemplified hereinbelow, provides a flexible thin layer cell which can be used as a power supply (i.e., a battery), which cell is open and therefore does not accumulate gases upon storage, yet the hygroscopicity of the deliquescent material ensures that the cell is kept wet at all times although open. Suitable pairs of materials to be used in negative 24 and positive 26 poles include, but are not limited to, manganese-dioxide/zinc; silver-oxide/zinc; cadmium/nickel-oxide; and iron/nickel-oxide (the manganese-dioxide and the silver-oxide are optionally mixed with a conductive carbon powder, as known in the art).

It is clear to one having ordinary skills in the art that a single material may function both as a deliquescent material and as the electroactive soluble material. Such a material should however acquire suitable electroactive and hygroscopic characteristics. Suitable materials of this type include, but are not limited to, zinc-chloride and zinc-bromide.

It is further clear to one having ordinary skills in the art that a single material may function as a deliquescent material and as a water-soluble polymer. Such a material should however acquire suitable hygroscopic and adhesive characteristics. Suitable materials of this type include, but are not limited to, dextrane, dextranesulfate and combinations and copolymers thereof.

The three layers 22, 24 and 26, presented in FIG. 2 and described hereinabove may be manufactured thin and are flexible, therefore cell 20 is flexible and as thin as about 0.3 or less to about 1.5 mm making it especially suitable for use with bandage 10.

Open cell 20 can be manufactured by a suitable printing technology including, but not limited to, silk print, offset print, jet printing, lamination, materials evaporation and powder dispersion.

Figure 3:
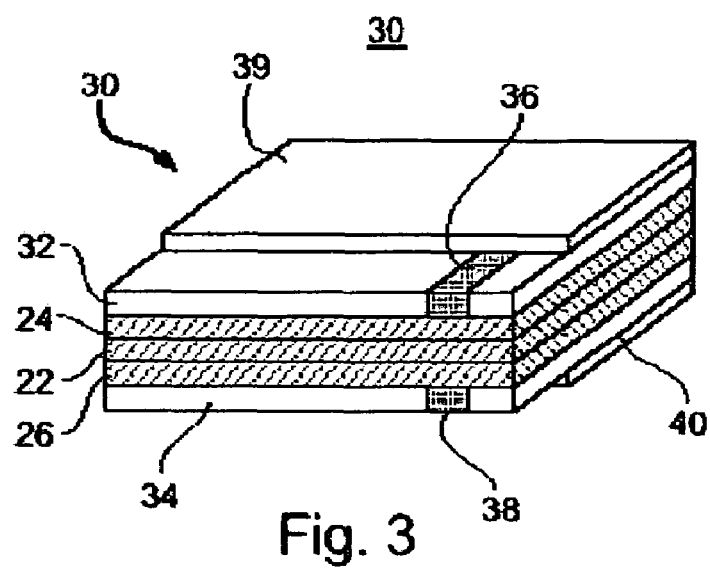
FIG. 3 is a perspective view of another possible configuration of a prior art flexible thin layer open electrochemical cell.

Another possible configuration of an open cell is shown in FIG. 3 illustrating a cell, generally assigned 30. As cell 20, cell 30 also includes layers 22, 24 and 26 (stripped region) forming a basic cell. Cell 30 further includes additional one or two conductive layers 32 and 34, to improve the electronic conductivity of negative 24 and/or positive 26 pole layers. Suitable conductive layers are graphite paper, carbon cloth, etc. Cell 30 also includes negative 36 and positive 38 terminals, which terminals 36 and 38 are in electrical contact with either the corresponding pole layer 24 and 26, respectively, or with the corresponding conductive layer 32 and 34, respectively, or both. Terminals 36 and 38 are made of any suitable materials such as, but not limited to, graphite or metals such as iron, nickel, titanium, copper, stainless steel and mixtures thereof, and are preferably applied to cell 30 by a suitable printing technology such as those listed above.

Terminals 36 and 38 are used to electrically connect cell 30 to display 18 of bandage 10. Terminals 36 and 38 may be located in any desired location of cell 30, may acquire any suitable shape and size and, depending on the specific configuration of bandage 10; terminals 36 and 38 may protrude from the surface and dimensions of cell 30. Cell 30 may further include at least one externally located adhesive backing 39, to enable attaching cell 30 to bandage 10, and/or at least one externally located lamina protective layer 40 to physically protect all other layers.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Reference is now made to the following examples, which together with the above descriptions, illustrate the invention in a non limiting fashion.

EXAMPLE 1

A child which has an open skin wound, which necessitates protection from dirt and bacteria may object to placing of a regular bandage due to, for example, fear of pain upon application of the bandage. The child will be more willing to apply the bandage with display of the present invention, due to the visual appeal of the display. The child can be encouraged to use the bandage of the present invention, especially if the visual effects are only possible once the bandage is applied to the wound.

EXAMPLE 2

An additional use of the bandage with display of the present invention is for detection and evaluation of skin condition. The skin condition display bandage is facile and easy to use and can be used by an individual with or without assistance from a trained professional.

The bandage with display is attached, preferably by the adhesive part of the bandage to the skin area of interest of the user. After attachment of the bandage with display, the display is activated by any suitable activation mode as specified hereinabove. Preferably, the bandage with display is kept attached to skin area until a signal alerts the user that skin condition evaluation is complete, or the bandage with display is kept attached for a prescribed time period. Optionally, a suitable signal can be a flashing light, a change in colour of display, a text message, a graphic display, a sound, such as an alarm or a combination thereof.

Preferably, the displayed skin condition value can then be used for prevention or determination of dermatological, cosmetic or medical treatment or as part of a treatment. Optionally, the bandage with display is disposable, reusable or for one-time use.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device comprising:
    (a) a bandage comprising a pad having a protective surface for covering a specific area of a body of a user, wherein the specific area is for treatment, protection or diagnosis;
    (b) an adhesive tape attached to said bandage, said adhesive tape being configured for attaching to a body region of a user so as to position said protective surface against a portion of said body region;
    (c) a display being positioned on an outer surface of the device, said display being configured for displaying a body condition of skin when said adhesive tape is attached to said body region, wherein said body condition is a skin condition selected from at least one of the group consisting of acidity (pH), moisture (water content), fat (sebum) content, elasticity, barrier function of skin (impermeability), skin resistance, skin conductance, scarring, pigmentation, melanin and erythrema index, transepidermal water loss, skin roughness, acne, bacteria, fungal and viral content and any combination thereof;
    (d) a body condition detector in contact with said body region and said display, said body condition detector being configured for detecting and evaluating said body condition; and
    (e) a power source attached to or integrated with said adhesive tape, said power source being for powering said display, said display being for increasing an acceptability of use of the device by the user when powered.

2. The device of claim 1, wherein said display includes at least one light emitting diode (LED).

3. The device of claim 1, wherein said power source is a thin layer electrochemical cell.

4. The device of claim 1, further comprising a sound device.

5. The device of claim 1, wherein said adhesive tape is reusable.

6. The device of claim 1, wherein said display is selected from at least one of the group consisting of all types of LCD display, polymer LCD display, LED display, VFD, fluorescent displays, organic displays, incandescent and neon display and illuminescence type display and any combination thereof.

7. The device of claim 1, wherein said bandage and the display are reusable.

8. The device of claim 1, wherein said pad is non-absorbent.

9. The device of claim 1, wherein said pad is absorbent.

10. The device of claim 1, wherein the power source is an open electrochemical cell.

11. The device of claim 1, for use in wound treatment.

* * * * *

UNITED STATES PATENT AND TRADEMARK OFFICE
CERTIFICATE OF CORRECTION

PATENT NO. : 7,652,188 B2  Page 1 of 1
APPLICATION NO. : 10/741435
DATED : January 26, 2010
INVENTOR(S) : Levanon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 392 days.

Signed and Sealed this

Twenty-third Day of November, 2010

David J. Kappos
*Director of the United States Patent and Trademark Office*